United States Patent [19]
Kelkenberg

[11] Patent Number: 5,004,564
[45] Date of Patent: Apr. 2, 1991

[54] N-ALKYLGLYCAMINO COMPOUNDS, A PROCESS FOR PRODUCING THEM, AND THEIR USE

[75] Inventor: Heike Kelkenberg, Gladbeck, Fed. Rep. of Germany

[73] Assignee: Huels Aktiengesellschaft, Marl, Fed. Rep. of Germany

[21] Appl. No.: 503,960

[22] Filed: Apr. 4, 1990

[30] Foreign Application Priority Data
May 9, 1989 [DE] Fed. Rep. of Germany ....... 3915121

[51] Int. Cl.$^5$ .......................... C11D 1/18; C11D 3/32; C11D 7/32; C07C 229/12
[52] U.S. Cl. ..................... 252/546; 252/548; 252/DIG. 13; 252/DIG. 5; 562/567
[58] Field of Search ............... 562/567; 252/546, 548, 252/DIG. 5, DIG. 13

[56] References Cited
U.S. PATENT DOCUMENTS

| | | | |
|---|---|---|---|
| 2,060,850 | 11/1936 | Calcott et al. | 260/127 |
| 2,060,851 | 11/1936 | Calcott et al. | 260/127 |
| 2,703,798 | 3/1955 | Schwartz | 260/211 |
| 2,781,388 | 2/1957 | Mannheimer | 260/548 |
| 2,781,391 | 2/1957 | Mannheimer | 260/459 |
| 2,786,869 | 3/1957 | Benneville et al. | 562/567 |
| 4,882,091 | 11/1989 | Kelkenberg et al. | 252/527 |

FOREIGN PATENT DOCUMENTS
586687 11/1959 Canada .

Primary Examiner—A. Lionel Clingman
Assistant Examiner—Erin M. Harriman
Attorney, Agent, or Firm—Oblon, Spivak, McClelland, Maier & Neustadt

[57] ABSTRACT

An N-alkylglycamino compound of formula (IV):

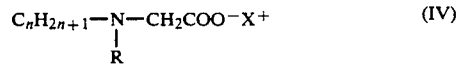

wherein n is 4–24,
R is

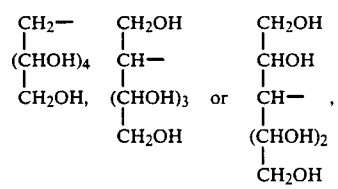

and x is Na, K, or H.

6 Claims, 5 Drawing Sheets

N-ALKYLGLYCAMINO COMPOUNDS, A PROCESS FOR PRODUCING THEM, AND THEIR USE

BACKGROUND OF THE INVENTION

1. Field of the Invention

The present invention relates to N-alkylglycamino compounds, a process for producing them, and their use.

2. Description of the Background

Renewable agricultural products are important raw materials for the detergent and personal care sectors. In addition to vegetable oils and animal fats, starch and monosaccharides are gaining increased importance. The first polyglycosides and saccharide esters are already available on the market as environmentally harmless surfactants. Glycamines based on monosaccharides likewise represent good starting materials for surface active detergents and personal care applications. Thus, for example, tertiary and quaternary fatty alkylglycammonium salts are mentioned as cationic detergents (U.S. Pat. Nos. 2,060,850; 2,060,851). Corresponding ethoxylated compounds are suggested as low-foam rinses and detergents as well as skin and hair conditioners (French Patent 1,573,085; German Disclosure 22 00 040, Japanese Patents 59-212,419, 59-212 421). Also known are nonionic surfactants based on fatty acid N-alkylglycamides, that are particularly gentle on the skin and at the same time have a thickening effect on shampoo and shower bath formulations (U.S. Pat. No. 2,703,798; German Disclosure 37 11 776).

Amphoteric surfactants represent a class of substances that behave like anionic or cationic surfactants depending on the adjustment of the medium (acidic, neutral, or alkaline), i.e., they have electronegative and electropositive groups combined in the same molecule. They are gaining increased importance in the personal care sector since they have particularly good skin tolerability and low toxicity, and show good effect in weakly acidic media as mild surfactants.

In general, the amphoteric surfactants are N-substituted amino acids of the following type (Formula I):

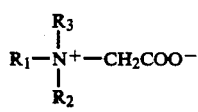

in which $R_1$ stands for a longer fatty alkyl chain and $R_2$, for example, stands for a shorter alkyl group. $R_3$ can represent either a proton or an alkyl group. There is a clear distinction between the behavior of amino acids having tetrasubstituted nitrogen and those having trisubstituted nitrogen. That is, tetrasubstituted amino acids, which are also called betaines (Formula II), have a fixed positive charge independently of the pH of the medium. In the neutral and alkaline ranges the isoelectric, zwitterionic character is retained. In the acidic range the betaine behaves like a cationic surfactant.

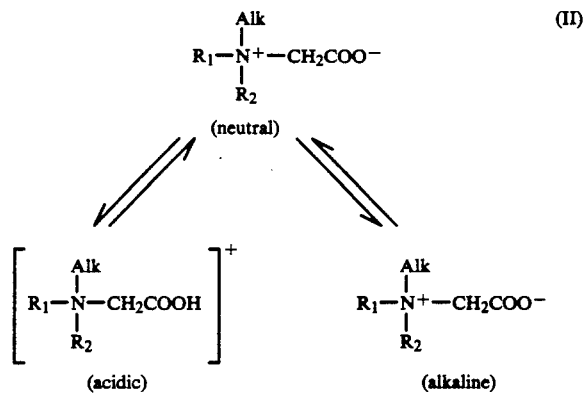

The trisubstituted amino acids (Formula III), on the other hand, represent real ampholytes.

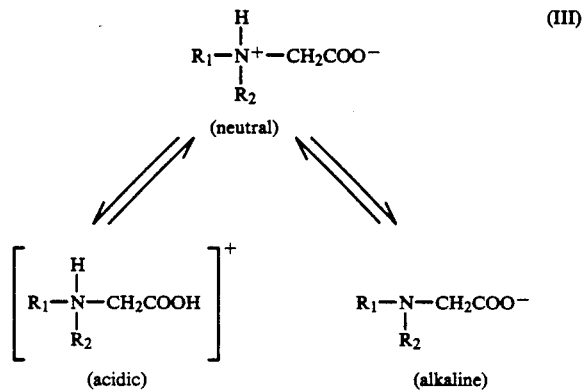

In the neutral range they form internal salts. In acidic media they change into cations, and in the alkaline range into anions.

A drawback of the known N-trisubstituted amphoteric surfactants is that in the desired pH range, specifically weakly acidic to neutral, they show a minimum in solubility, foaming power, and wetting power when used in formulations which are employed in the personal care sector such as shampoos and shower materials [Tenside Detergents 23 (1986) 309]. A need therefore continues to exist for N-trisubstituted amphoteric surfactants which exhibit improved surfactant properties.

SUMMARY OF THE INVENTION

Accordingly, one object of the present invention is to provide improved N-trisubstituted amphoteric surfactants based on monosaccharides, as renewable raw materials which show improved solubility, foaming power and wetting power.

Briefly, this object and other objects of the present invention as hereinafter will become more readily apparent can be attained by a glycamino-acetic acid/acetate of formula (IV):

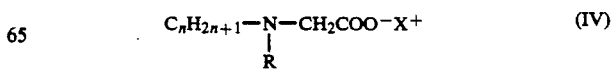

wherein n is 4–24, R stands for

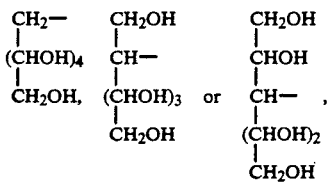

and X stands for Na, K, or H.

BRIEF DESCRIPTION OF THE DRAWINGS

A more complete understanding of the invention and many of the attendant advantages there of will be readily obtained as the same becomes better understood by reference to the following detailed description when considered in connection with the accompanying drawings, wherein.

DETAILED DESCRIPTION OF THE PREFERRED EMBODIMENTS

Figure 1:
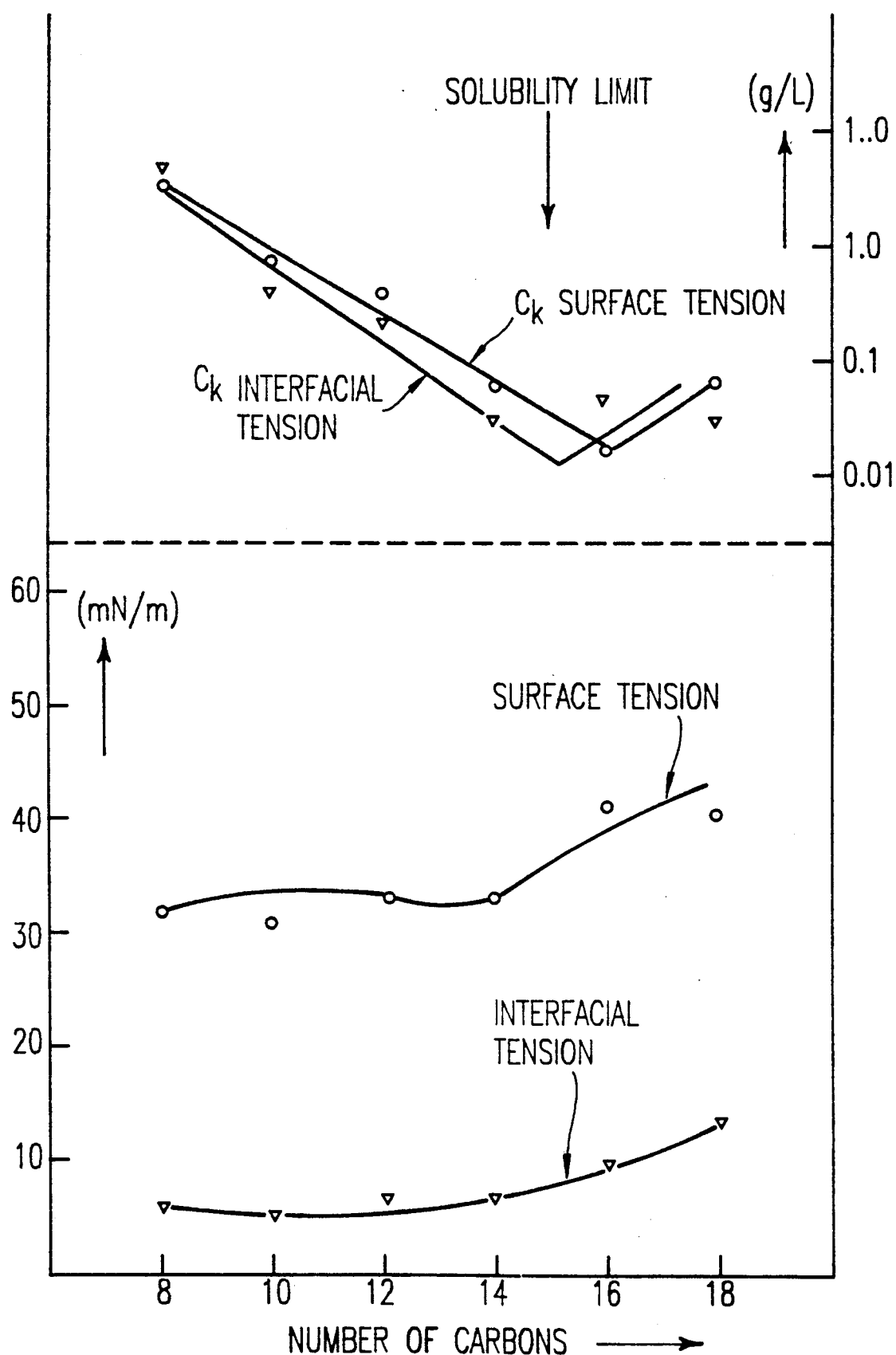
FIG. 1 shows the results of the measurement of interfacial tension, of surface tension and of critical micelle concentration of aqueous alkylglucaminoacetate solutions.

Suitable examples of N-alkyl-N-(desoxyhexityl) acetic acid salts having Formula (IV)

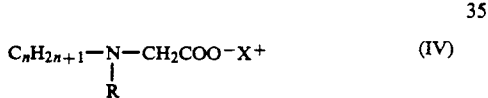

include those in which n is 4–24, preferably 8–14, and R preferably is a desoxyhexityl group such as, for example, 1-desoxy-1-glucityl-, 2-desoxy-2-glucityl-, 3-desoxy- 3-glucityl-, 1-desoxy-1-mannityl, 2-desoxy-2-mannityl-, 3-desoxy-3-mannityl-, 1-desoxy-1-dulcityl-, 2-desoxy-2-dulcityl-, 3-desoxy-3-dulcityl-, 1-desoxy-1-allityl-, 2-desoxy-2-allityl-, 3-desoxy-3-allityl-, 1-desoxy-1-altrityl-, 2-desoxy-2-altrityl-, 3-desoxy-3-altrityl-, 1-desoxy-1-talityl-, 2-desoxy-2-talityl- or 3-desoxy-3-talityl-. Preferably, R is a 1-desoxy-1-glucityl group, and X is Na.

It has not been found surprisingly that the trisubstituted amphoteric compounds of formula IV of the present invention have outstanding surfactant properties. In comparison with trisuibstituted amphoteric surfactants of formula III, they have good water solubility. The trisubstituted amphoteric surfactants of the present invention also show good skin tolerability. The $C_{12}$-alkylglucamino acetate in particular shows exceptional properties which include no opalescence over the entire pH range from 2 to 12 and good solubility such that clear solutions are formed.

Chemical compounds of formula IV are prepared by carboxymethylation of N-alkylglycamines, for example, N- alkyl-1-amino-1-desoxyhexitols, by generally known procedures depending on the solubility of the amine in water or butanol as solvent. By maintaining a pH of 8 –9 by continuous addition of alkali such as an alkali metal hydroxide of which sodium hydroxide is preferred, and maintaining a reaction temperature below 80° C., selective N-carboxymethylation is achieved without the OH groups of the hexityl structure reacting.

The N-alkylglycamines themselves are prepared by generally familiar procedures of reductive amination of monosaccharides (U.S. Pat. Nos. 1,994,467; 2,016,962), particularly hexoses with alkylamines such as butylamine, octylamine, laurylamine, myristylamine, stearylamine, or coco fatty amine, with the following being mentioned as examples of monosaccharides: glucose, galactose, mannose, fructose, allose, altrose, talose, and glucose syrup.

The N-alkylglycamino compound of the present invention is normally incorporated in a detergent formulation in an amount ranging from 2 to 50% by wt, preferably 10–30% by wt. The N-alkylglycamino compound of the invention can be combined with other surfactants including ether carboxylates, nonionic surfactants, amine oxide compounds, paraffin sulfonate compounds, sulfosuccinic acid semi-esters and the like. The detergent formulations include other additives such as thickeners, fatty acid diethanol amides and preservatives.

The present N-alkylglycamino compound is particularly useful in the preparation of formulations used in the body and hair, such as in bubble bath and hair shampoos where mild detergent formulations are needed.

Having now generally described this invention, a further understanding can be obtained by reference to certain specific examples which are provided herein for purposes of illustration only and are not intended to be limiting unless otherwise specified.

Preparation of Salts

1. Octylglucaminoacetic acid, Na salt

A 19.4 g (0.205 mole) amount of chloroacetic acid is dissolved in 106.2 g (5.9 moles) of water and 58.6 g (0.2 mole) of octylglucamine is added in portions with stirring. At the same time the temperature is raised to 60° C.. After the octylglucamine has dissolved completely, 102.4 g (88 ml, 0.409 mole) of a 16% sodium hydroxide solution is added dropwise at a pH between 8 and 9. Toward the end of the reaction the temperature is raised to 65° C.. After the sodium hydroxide has been completely added, the mixture is allowed to react for 1 hour at 70° C. The unreacted octylglucamine precipitates in the cold (6.5 g, m.p.: 121°–123° C., alkali number: 183.6 mg KOH/g), and is removed by filtration. The filtrate is then evaporated to dryness.

| | |
|---|---|
| Yield: | 78.6 g (83.2%) |
| Melting range: | 80–154° C. |
| Nitrogen content: | 3.01% (3.75%) |
| Carboxyl number: | 121 mg KOH/g |
| Purity: | 79% octylglucamino-acetic acid Na-salt ($^{13}$C NMR) |
| | 6% Na glycolate |
| | 15% NaCl |

2. Decylglucaminoacetic acid, Na-salt

A 19.4 (0.205 mole) amount of chloroacetic acid is dissolved in 192.6 g (2.6 moles) of n-butanol and 64.2 g (0.2 mole) of decylglucamine is added in portions with stirring. The temperature is raised to 60° C. After the decylglucamine has completely dissolved, 102.4 g (88 ml, 0.409 mole) of a 15% sodium hydroxide solution is added dropwise at a pH between 8 and 9. Toward the end of the reaction the temperature is raised to 65° C.. After completing the addition of sodium hydroxide solution, the mixture is allowed to react for 1 hour at 70° C.. The water is then removed by distillation azeotropically with continuous addition of n-butanol. NaCl precipitates, and is filtered while the solution is hot. A white precipitate separates from the filtrate in the cold. The separated precipitate is dissolved in hot water in a 1:3 ratio and is then cooled. The unreacted decylglucamine precipitates (2.5 g, m.p.: 122°–123° C., alkali number: 170 mg KOH/g) and is removed by filtration. The filtrate is evaporated to dryness.

| Yield: | 67.4 g (84%) |
|---|---|
| Melting range: | 95–171° C. |
| Nitrogen content: | 3.25% |
| Carboxyl number: | 132.0 mg KOH/g |
| Purity: | 92.7% decylglucamino-acetic acid Na-salt ($^{13}$C NMR) |
| | 2.6% decylglucamine |
| | 4.2% Na glycolate |
| | 0.51 NaCl |

3. Dodecylglucaminoacetic acid, Na-salt

Chloroacetic acid is reacted with dodecylglucamine by the same method described in Example 2.

| Yield: | 71.5 g (83.3%) |
|---|---|
| Melting point: | 172–174° C. |
| Nitrogen content: | 3.07% |
| Carboxyl number: | 115.3 mg KOH/g |
| Purity: | 96.0% dodecylgluca-minoacetic acid Na-salt ($^{13}$C NMR) |
| | 2.4% Na qlycolate |
| | 1.6% NaCl |

4. Tetradecylglucaminoacetic acid, Na-salt

Chloroacetic acid is reacted with tetradecylglucamine by the same method described in Example 2.

| Yield: | 94.9 g (97.8%) |
|---|---|
| Melting range: | 160–162° C. |
| Nitrogen content: | 2.88% |
| Carboxyl number: | 111.6 mg KOH/g |
| Purity: | 97.8 & tetradecylgluca-minoacetic acid Na-salt ($^{13}$C NMR) |
| | 1.8% Na glycolate |
| | 0.4% NaCl |

5. Hexadecylglucaminoacetic acid, Na-salt

Chloroacetic acid is converted with hexadecylglucamine by the same method described in Example 2.

| Yield: | 95 g (97.8%) |
|---|---|
| Melting range: | 90–162° C. |
| Nitrogen content: | 2.83% |
| Purity: | 85.3% hexadecylgluca-minoacetic acid Na-salt ($^{13}$C NMR) |
| | 12.0% hexadecylglu-camine |
| | 2.3% Na glycolate |
| | 0.35% NaCl |

6. Octadecylglucaminoacetic acid, Na-salt

Chloroacetic acid is reacted with octadecylglucamine by the same method described in Example 2.

| Yield: | 91.8 g (89.5%) |
|---|---|
| Melting range: | 75–132° C., 210° C. dec. |
| Nitrogen conetne: | 3.72% |
| Purity: | 83.6% octadecylgluca-minoacetic acid Na-salt ($^{13}$C NMR) |
| | 12.8% octadecylglu-camine |
| | 3.3% Na glycolate |
| | 0.30% NaCl |

Examples of surfactant compositions and their properties

7. Interfacial/surface tension and critical micelle concentration

The alkylglucaminoacetates in which n=8, 10, 12, 14, 16, and 18, synthesized as described above were measured as 1% aqueous solutions after adjusting the pH to 5.6.

FIG. 1 shows the results of the measurement of interfacial tension and of surface tension (bottom of the illustration) and of the critical micelle concentration with a Lauda Tensiometer (top of the illustration), measured against air or paraffin by the du Noüy ring method.

In their surface-active properties, the glucaminoacetates show conventional behavior with respect to the lowering of surface and interfacial tension. For comparison, the surface and interfacial tension and the critical micelle concentration of carboxymethyldimethylcocoammonium betaine (R-N$^+$ (CH$_3$)$_2$—CH$_2$COO$^-$ in which R=C$_{12}$–C$_{14}$), a commercial betaine, were determined (see Table 1).

TABLE 1

| Surface/interfacial tension and critical micelle concentration (cmc) | | | | |
|---|---|---|---|---|
| | Surface tension (20° C.; in cd water) | | Interfacial tension (20° C., versus paraffin) | |
| | cmc (g/l) | ST (mN/m) | cmc (g/l) | IT (mN/m) |
| Dodecylglucamino-acetic acid | 0.37 | 33.0 | 0.22 | 5.8 |
| Tetradecylglu-minoacetic acid | 0.058 | 32.8 | 0.03 | 5.8 |
| Betaine | 0.04 | 33.2 | 0.61 | 3.2 | cd = completely deionized water

8. Foaming power

Figure 2A:
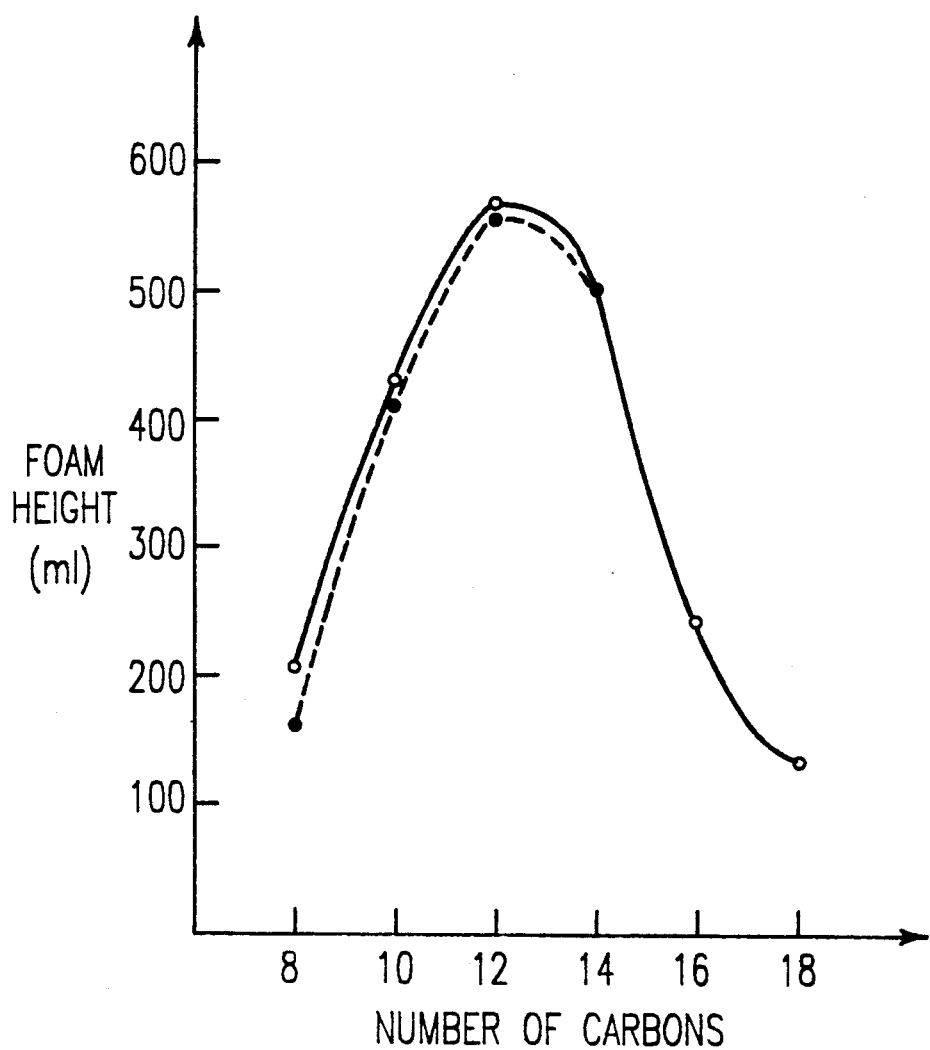
FIG. 2a–2c show the foaming power of aqueous solution of alkylglucaminoacetates of Example y.
Figure 2C:
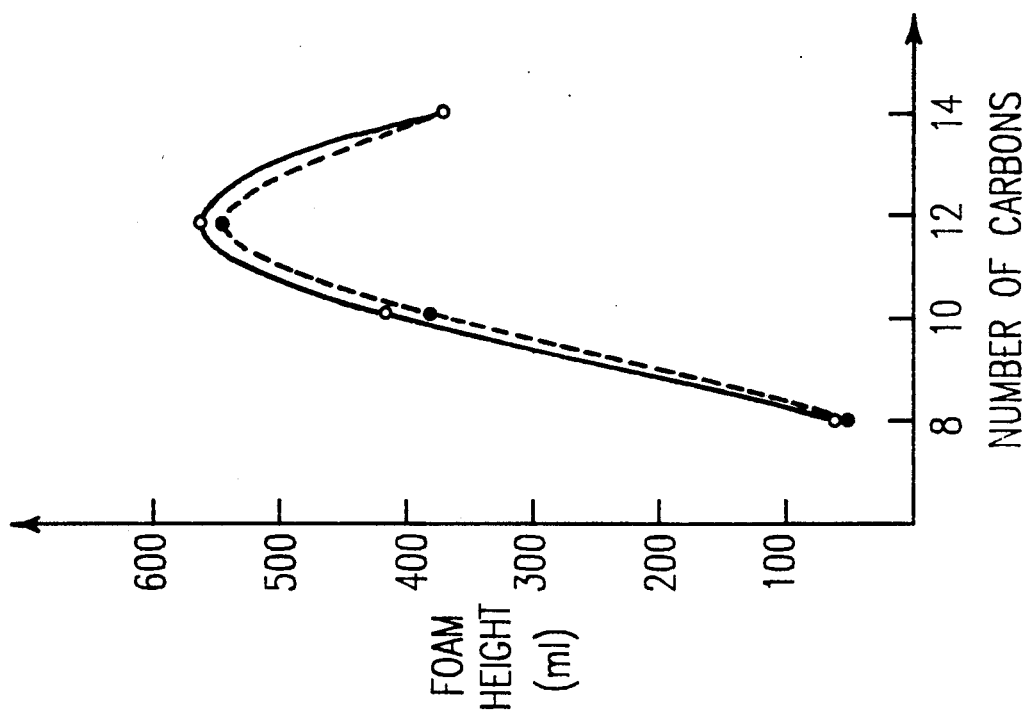
Figure 2B:
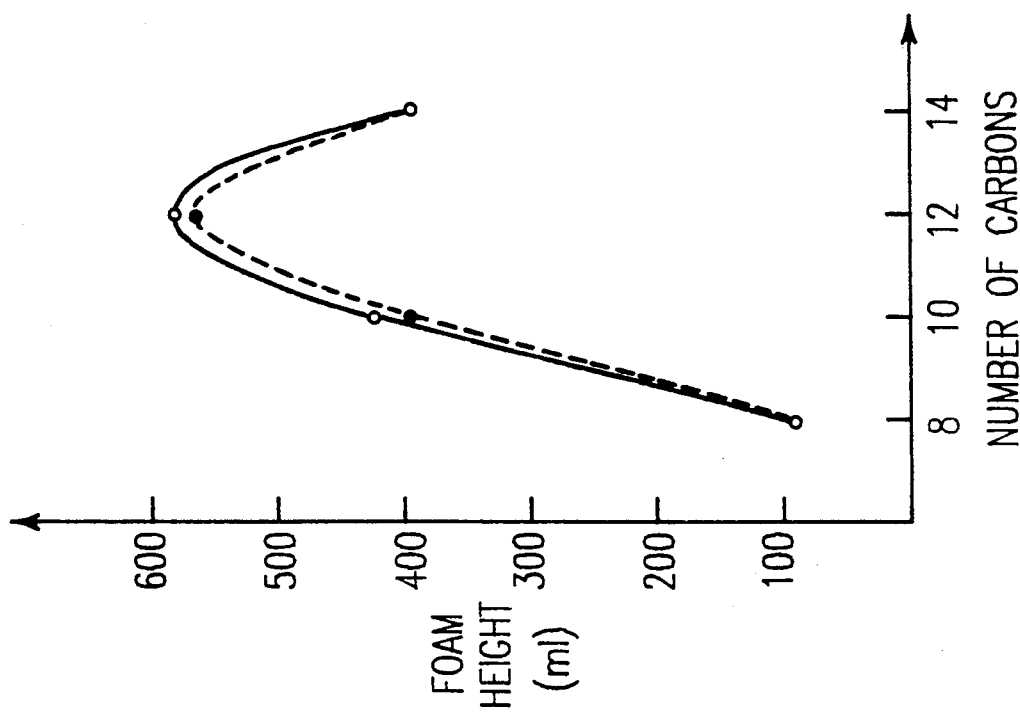

The foaming power of the alkylglucaminoacetates of Example 7 were measured according to DIN 53 902 as 0.1% aqueous solutions with pH adjustments of 9.9±0.3; 7.00, and 5.60. At pH 7.00 and 5.60 the C$_{16}$ and C$_{18}$ glucaminoacetic acids show inadequate solubility. The results are shown in FIGS. 2a (for pH 9.9±0.3), 2b (for pH 7.00), and 2c (for pH 5.6). Each of the solid lines means the values after 30 seconds and the broken curve means the values after 300 seconds.

The maximum foaming power was reached with the dodecylgluicaminoacetate. The values produced (readings after 30 s/300 s) of 580 ml/560 ml are comparable with those of the commercial anionic surfactant (MAR- LON ® A: alkylbenzenesulfonate) of 590 ml/570 ml, and are distinctly higher than those of the ether sulfate (MARLINAT ® 242: $C_{12-14}$ with 2.2 EO) with 540 ml/540 ml and of carboxymethyldimethylcocoammonium betaine with 510 ml/500 ml.

In spite of the ampholytic nature of the alkylglucamino compounds, no pH dependency can be observed.

Figure 3:
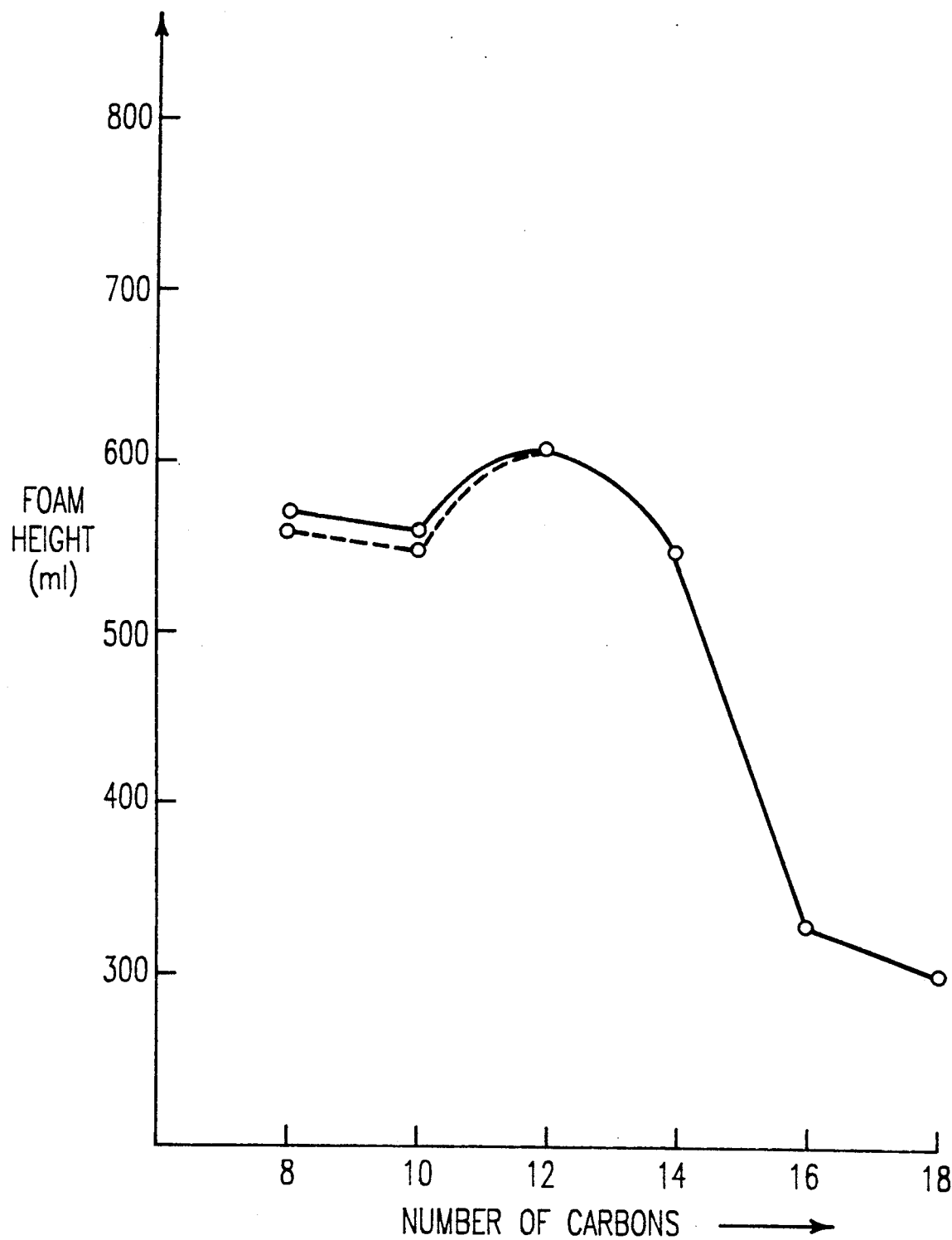
FIG. 3 shows the foaming power of mixed surfactant-alkylglucaminoacetates.

By mixing the alkylglucamino compounds with the surfactant MARLINAT ® 242 the foaming power of the short-chained alkylglucamino-acetic acids can be increased distinctly. The maximum is likewise reached with dodecylglucaminoacetate (see FIG. 3: measured at pH 5.60, solid line shows values after 30 seconds, broken line values after 300 seconds).

9. Wetting power on hair

The use of a surfactant in shampoos assumes good wetting of the hair. To evaluate the wetting, the wetting angle between a partly immersed hair and the surface of the surfactant solution was used [Colloids and Surfaces 6 (1983) 49–61]. Dodecylglucaminoacetic acid Na salt as a 0.1% surfactant solution at pH 6, based on water, shows a wetting angle reduction of 53.8%.

10. Skin tolerability

Figure 4:
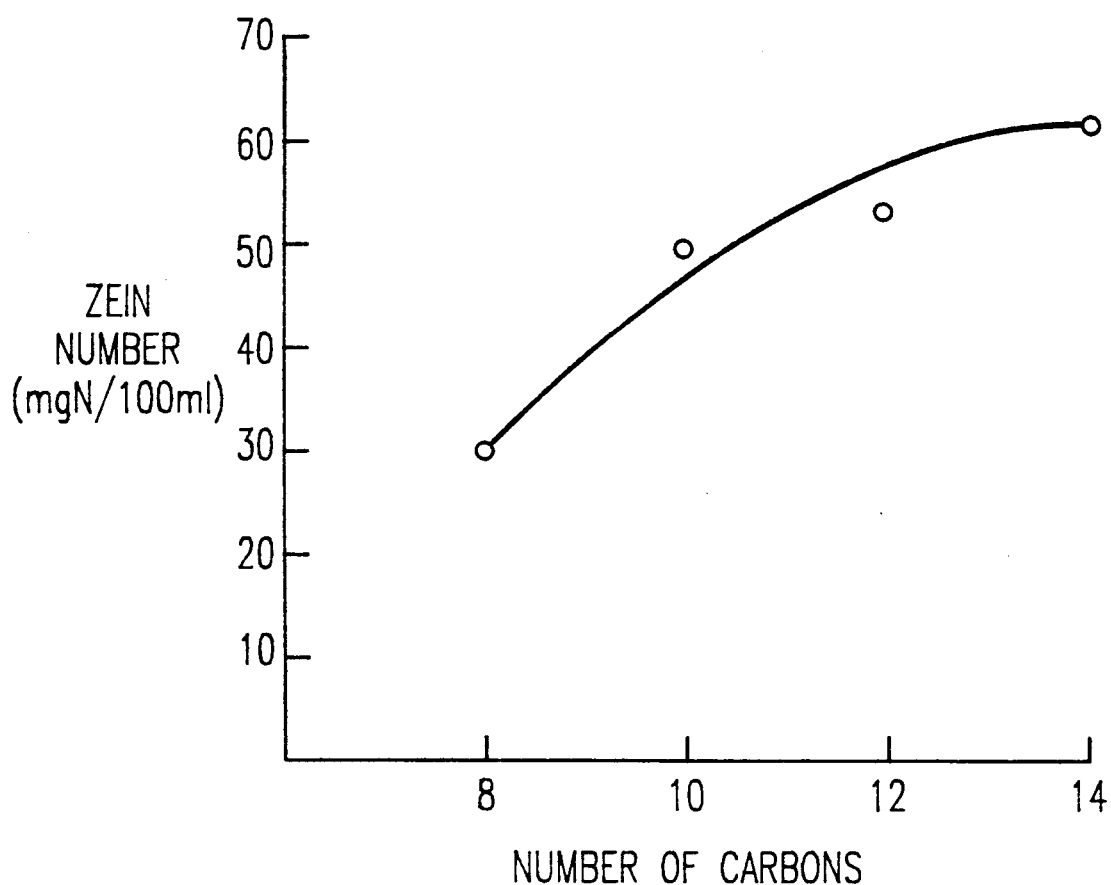
FIG. 4 shows the skin tolerability of aqueous solutions of the alkylglucamino-acetate acid Na salts of Examples 1 to 4.

Skin tolerability was determined by the Gotte zein test (CID Brussels 1984, 83–90). FIG. 4 shows the results for the alkylglucamino-acetic acid Na salts of Examples 1 to 4 in 1% aqueous solution at pH 5.6. The zein numbers found indicate very good skin tolerability. They are clearly below the value of the commercial anionic surfactant MARLON ® A of 510 mg N/100 ml and are comparable with those of the betaines, with which zein numbers of about 50 mg N/100 ml are achieved.

11. Hair shampoo formulation

The table below provides a comparison between a formulation within the scope of the present invention (No. 2) and a conventional formulation (No. 1) which does not contain the N-alkylglycamino compound of the invention.

| | Application example: | |
|---|---|---|
| components | shampoo 1 | shampoo 2 |
| Marlinat 242 (w = 0.28) | 13.9 | 13.9 |
| ampholyte JP 130 (w = 0.30) | 17.8 | — |
| glucamine-Na-salt (w = 0.4) | — | 11.4 |
| Bervoxyl VLB 1132 (w = 0.4) | 11.4 | 11.4 |
| Dionil OC | 2.0 | 2.0 |
| Lamepon S | 2.0 | 2.0 |
| remainder | | |
| conventional additives | 0.62 | 2.62 |
| water | ad 100 | ad 100 |
| properties | | |
| foam capacity at 20° C. | [ml] after | [ml] after /illegible/ |
| cd water | 540/525 | 540/555 |
| drinking water | 425/405 | 480/460 |
| viscosity at 20° C. [mPas] | 2605 | 3002 |

Marlinat 242 = 28% coconut butter alcohol - 2 EO - sulfate Na-salt
ampholyte JP 130 = 30% coconut butter acid - amidopropylbetaine
glucamine-Na-salt = N-dodecyl-N-carboxymethyl-glucamine-Na-salt
Servoxyl VLB 1123 = 40% lauryl - 3 EO - sulfosuccinate-Na
Dionil OC = oleic acid monoethanolamide = 3 EO
Lamepon ® S = protein fatty acid condensate

Having now fully described the invention, it will be apparent to one of ordinary skill in the art that many changes and modifications can be made thereto without departing from the spirit or scope of the invention as set forth herein.

What is claimed as new and is intended to be secured by Letters Patent of the United States is:

1. An N-Alkylglycamino compound of formula (IV):

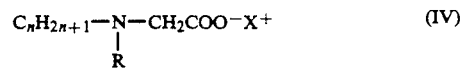

wherein n is 8–24,
R is

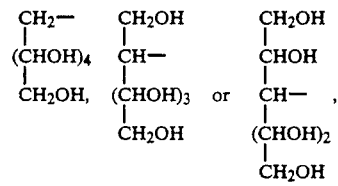

and x is Na, K, or H.

2. The N-alkylglycamino compound of claim 1, wherein n is 8–14.

3. The N-alkylglycamino compound of claim 1, wherein A is:

4. The N-alkylglycamino compound of claim 1, wherein X is Na.

5. A cleansing formulation comprising from 2 to 50% by wt of the N-alkylglycamino compound of claim 1 in combination with other cleansing formulation ingredients.

6. The cleansing formulation of claim 5, wherein said formulation is a hair shampoo or bubble bath.

* * * * *